United States Patent [19]
Burke, Jr. et al.

[11] Patent Number: 5,169,862
[45] Date of Patent: Dec. 8, 1992

[54] ANALOGS OF VISCOSIN AND THEIR USES

[75] Inventors: Terrence Burke, Jr., Bethesda; Bhaskar Chandrasekhar, Silver Spring; Martha Knight, Bethesda, all of Md.

[73] Assignee: Peptide Technologies Corporation, Washington, D.C.

[21] Appl. No.: 793,153

[22] Filed: Nov. 18, 1991

Related U.S. Application Data

[62] Division of Ser. No. 376,556, Jul. 7, 1989, abandoned.

[51] Int. Cl.$^5$ ................ A61K 31/335; C07D 323/00
[52] U.S. Cl. ................................ 514/450; 549/351; 530/321; 530/328; 562/564; 562/577
[58] Field of Search .................... 549/351; 514/450

[56] References Cited

FOREIGN PATENT DOCUMENTS 62-263176  11/1987  Japan .

OTHER PUBLICATIONS

Shinkai et al., JACS, 109, 4458–4464 (1987).
Anwer et al., *Synthesis* 929–932 (1980).
Boné et al., *J. Gen. Microbiol*, 31:261–266 (1963).
Carpino et al., *J. Amer. Chem. Soc.* 92:5748–5749 (1970).
Cunningham et al., *J. Gen. Micro.* 70:491–496 (1972).
Fonken et al., *J. Amer. Chem. Soc.* 74:831–833 (1952).
Groupé et al., *Proc. Soc. Exptl. Biol. Med.* 78:354–358 (1951).
Gaur et al., *Indian J. Chem.* 27B:405–408 (1988).
Godfrey, *Exp. Parasitology* 7:255–268 (1958).
Hiramoto et al., *Tetrahedron Lett.* 13:1087–1090 (1970).
Hiramoto et al., *Biochem. Biophys. Res. Comm.* 35(5):702–706 (1969).
Horton et al., *Antimicrobial Therapy*, eds. A. M. Ristuccia and B. A. Cunha, Raven Press, New York, pp. 329–334 (1984).
Jaynes et al., *FASEB J.* 2:2878–2883 (1988).
Kisfaludy et al., *Synthesis* pp. 325–327 (1983).
Kochi et al., *Gen. Bacteriology* pp. 29–30 (1951).
Mercado et al., *Antimicrobial Agents and Chemotherapy* 22(6):1051–1057 (1982).
Ouaissi et al., *Science* 234:603–607 (1986).
Paine et al., *J. Org. Chem.* 41(24):3857–3860 (1976).
Rinehart et al., *J. Am. Chem. Soc.* 109:6846–6848 (1987).
Rosenthal et al., *Antimicrobial Agents and Chemotherapy* 12(6):665–672 (1977).
Storm et al., *Ann. Rev. Biochem.* 46:723–63 (1977).
Shemyakin et al., *Experentia* 19:566–568 (1963).
Timm et al., *Comp. Biochem. Physiol.* 71B(3):397–402 (1982).
Ungaro et al. *J. Amer. Chem. Soc.* 98:5198–5202 (1976).
Vining et al., *Can. J. Chem.* 40:1579–1584 (1962).
Yagi et al., *J. Incl. Phenomena* 2:179–184 (1984).
Pedersen, *Science* 241:536–540 (1988).

*Primary Examiner*—Nicky Chan
*Attorney, Agent, or Firm*—Sterne, Kessler, Goldstein & Fox

[57] ABSTRACT

This invention is directed to the analogs of viscosin, pharmaceutical compositions thereof and to their use as antibacterial, antiviral and antitrypanosomal therapeutic compounds.

2 Claims, No Drawings

ANALOGS OF VISCOSIN AND THEIR USES

This application is a division of application Ser. No. 07/376,556 filed Jul. 7, 1989, now abandoned.

FIELD OF THE INVENTION

This invention is in the field of pharmaceutical compounds, specifically directed to analogs of viscosin and to their uses as antibacterial, antiviral and antitrypanosomal therapeutic compounds.

BACKGROUND OF THE INVENTION

Trypanosomal diseases include some of the most pervasive and problematic illnesses facing man today. Of these, Chagas' disease, which is concentrated principally in Central and South America, is of particular concern, both for the number of individuals infected and for the lack of adequate chemotherapy to treat the disease (Brener, Z., *Bull. WHO* 60:463 (1982); Hammond et al., *Trans. Royal Soc'y Trop. Med. Hyg.* 78:91 (1984)). Although estimates of the extent of the disease vary, it is generally agreed that in excess of 10 million people are presently infected, representing in some reporting areas up to 43% of the total population. While the causative agent for Chagas' disease, *Trypanosoma cruzi*, is transmitted predominantly in rural areas by the reduviid bug, the disease is finding its way into urban areas through blood transfusion (Brener, A., *Pharmacol. Ther.* 7:71 (1979)). Chagas' disease is not presently a problem in North America, with only a few cases of indigenous Chagas' disease having been reported in the United States. However, *T. cruzi* is found in mammals and insects across the southern United States, as far north as Virginia (Downs, W. G., *J. Parasit.* 49:50 (1963)).

Although two agents which abolish parasitemia in the acute phase are presently available (*Nifurtimox:* (3-methyl-4-(5-nitrofurfurylidineamino) tetrahydro-4H-1,4-thiazine-1,1-dioxide) and *Benznidazole:* (N-benzyl-2-nitro-1-imidazoleacetamide)) (Keierszenbaum, F., *Trop. Med Parasit.*, Mansfield ed., Marcel Dekker, New York (1984)), neither results in complete cure and both have serious side effects. Because of toxicity and the inability to completely abolish parasitemia with certainty, these drugs are not recommended as treatments for populations with chronic Chagas' disease. The unavailability of adequate chemotherapeutic agents for the treatment of Chagas' disease underlies the need for research of new antichagasic drugs.

SUMMARY OF THE INVENTION

In an effort to develop new leads in the treatment of Chagas' disease, the inventors analyzed the metabolic products of the Pseudomonas species. An antitrypanosomal factor had previously been discovered from *P. fluorescens*, which proved to be lytic towards *T. cruzi*. The inventors studies the peptide lactone viscosin, which had been shown to have antiviral and antimicrobial activity against various mycobacteria. Preliminary in vitro testing against *T. cruzi* produced trypanosomal lysis in the absence of significant hemolysis. This result was subsequently supported by promising in vivo activity in mice. To pursue these initial indications, viscosin and a number of analogs were prepared by solid-phase peptide synthesis in an effort to define structural characteristics favorable to anti-cruzi activity. This invention is directed to the analogs of viscosin, pharmaceutical compositions thereof and to their use as antibacterial, antiviral and antitrypanosomal therapeutic compounds.

DETAILED DESCRIPTION OF THE INVENTION

Viscosin is a peptide lactone composed of alternating D and L amino acids with a $\beta$-D-hydroxydecanoyl dipeptide side chain. This peptide has antibacterial, antiviral and antitrypanosomal activity against *Tyrpanosoma cruzi*, the pathogen involved in the South American Chagas' disease. The synthesis by solid phase methods utilizing an acid sensitive resin and a combination of Fmoc/Boc amino protection is described in Example 1.

In an effort to develop antichagasic agents based on viscosin, a series of analogs were prepared which were synthetically more accessible. One aspect of this invention involves alteration of the peptide side chain and ring junction. Side chain analogs consist of a variety of linear alkyl amides while modifications in the ring junction involve replacing the D-allo-Thr with D-Thr. Synthesis of these analogs is based on those techniques used to prepare viscosin itself, and rely on the novel use of activated esters of pentafluorophenol for the coupling of unprotected hydroxyl-bearing amino acids.

A second aspect of this invention addresses the rate of ion transport in viscosin's anticruzi activity and involves replacement of the peptide lactone ring with a crown ether. In general, any crown ether that has ionophore properties may be substituted for the peptide lactone ring of viscosin. Preferable crown ethers include benzo-15-crown-5 polyether, dibenzo-18-crown-6 polyether, dibenzo-24-crown-8 polyether, 2-hydroxymethyl-12-crown-4, 2-hydroxymethyl-15-crown-5 polyether, and 2-hydroxymethyl-18-crown-6 polyether. A most preferable crown ether is benzo-15-crown-5 polyether. These analogs may further differ from each other in the side chain R which are long chain alkylamides or simple peptides.

The viscosin analogs comprising crown ethers may be prepared according to the general methods of synthesis set forth in the examples section of the application. For example, where the crown ether is fused to a benzene ring, it is possible to nitrate the ring with nitric acid, followed by reduction to give the amine followed by the condensation thereof with an appropriate side chain precursor to give the viscosin derivative.

Viscosin is a cyclic depsipeptide with the following formula:

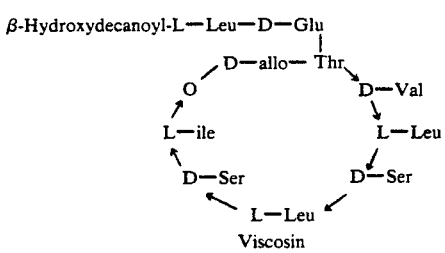

Viscosin

Cyclic peptide analogues of this invention may have the following Formula I:

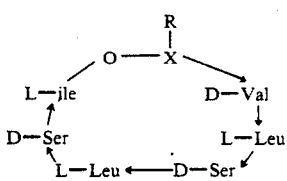

wherein X is D-allo-Thr, D-Thr, D-Ser, or HomoSer and wherein R is D-3-hydroxydecanoyl-L-Leu-D-Glu, Decanoyl-L-Leu-D-Glu, Octadecanoyl, $C_2$ to $C_{22}$ linear alkyl amides, D-3-hydroxydecanoyl-L-$X_1$-$X_2$, wherein $X_1$ is Ile, Val, Gly, or NorIle and wherein $X_2$ is D-Asp, D-γGlu, D-βAsp, Succinic acid, or dicarboxylic acid, provided that X is not D-allo-Thr when R is D-3-hydroxydecanoyl-L-Leu-D-Glu.

The cyclic peptide analogues of this invention may also be a subset of Formula I, which have the following Formula IA:

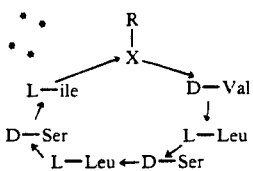

wherein X is D or L Lys or Ornithine, and wherein R is D-3-hydroxydecanoyl-L-Leu-D-Glu, Decanoyl-L-Leu-D-Glu, Octadecanoyl, $C_2$ to $C_{22}$ linear alkyl amides, D-3-hydroxydecanoyl-L-$X_1$-$X_2$, wherein $X_1$ is Ile, Val, Gly, or NorIle and wherein $X_2$ is D-Asp, D-γGlu, D-βAsp, Succinic acid, or dicarboxylic acid.

Linear analogues of this invention may have the following Formula II:

D-3- hydroxydecanoyl-L-Leu-D-Glu-X-D-Val-L-Leu-D-Ser-L-Leu-D-Ser-L-Ile-OH wherein X is D-allo-Thr; or D-3-Hydroxydecanoyl-L-Leu-D-Glu-HN$_2$; or

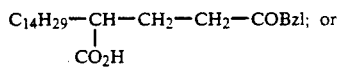

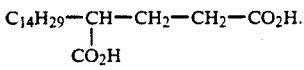

Peptidomimetics or "crown ether" analogues of this invention have the following Formula III:

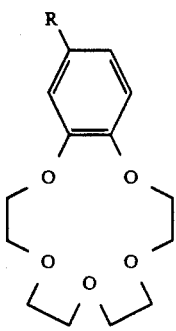

Formula III wherein R is
D-3-Hydroxydecanoyl-L-Leu-OBzl-D-Glu-NH;
D-3-Hydroxydecanoyl-L-Leu-D-Glu-NH;
Decanoyl-L-Leu-OBzl-D-Glu-NH;
Decanoyl-L-Leu-D-Glu-NH;

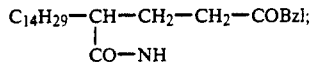

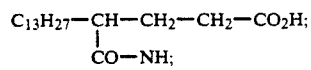

AcNH;
$C_3$-$C_{22}$ linear alkyl amides;
D-3-hydroxydecanoyl-L-$X_1$-D-$X_2$-NH or
Decanoyl-L-$X_1$-D-$X_2$-NH, wherein $X_1$ is a neutral amino acid and wherein $X_2$ is an acidic or a neutral amino acid.

As is known in the art, amino acid substitutions may be made to modulate finely the characteristics of the analogues, provided the analogue still has biological activity. Thus, original residue Leu may be substituted with Ile or Val; original residue Val may be substituted with Ile or Leu; original residue Ser may be substituted with Thr; original residue Ile may be substituted with Leu or Val; and original residue Thr may be substituted with Ser.

The peptide analogs of this invention have antichagasic activity. Thus, these analogs are useful as therapeutic compounds for typanosomal mediated diseases, such as Chagas' disease. These analogs also have other antimicrobial activity as well. Importantly, these analogs also have antiviral activities. Of particular interest is the use of these analogs as a topical therapeutic in treating skin lesions, such as those caused by Herpes Simplex and Herpes Complex.

The dose ranges for the administration of the viscosin analogs of the invention are those which are large enough to produce the desired effect whereby the symptoms of bacterial, viral or trypanosomal infection are ameliorated. The dosage should not be so large as to cause adverse side effects, such as unwanted cross-reactions, anaphylactic reactions, and the like, Generally, the dosage will vary with the age, condition, sex and extent of disease in the patient, counter indications, if any, immune tolerance and other such variables, to be adjusted by the individual physician. Dosage can vary from 0.01 mg/kg to 10 mg/kg, preferably, 0.01 mg/kg to 0.1 mg/kg, of the viscosin analogs of the invention in one or more administrations daily, for one or several days. The viscosin analogs of the invention can be administered parenterally by injection or by gradual perfusion over time. They can also be administered intravenously, intraperitoneally, intramuscularly, subcutaneously or by inhalation.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate, Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils, Intravenous vehicles include fluid and nutrient replenishers, electrolyte replenishers, such as those based on Ringer's dextrose, and the like. Preservatives and other additives may also be present, such as, for example, antimicrobials, antioxidants, chelating agents, inert gases and the like. See, generally, *Remington's Pharmaceutical Science*, 16th Ed., Mack Eds., 1980.

The invention also relates to a method for preparing a medicament or pharmaceutical composition comprising the components of the invention, the medicament being used for therapy of bacterial, viral, and trypanosomal infection in animals.

An exemplary list of causative agents for diseases and conditions that may be treated by the analogues of this invention include microbes and protozoa, such as *Bacteroides fragilis*, Fusobacterium spp., *Bordetella pertussis, Haemophilus influenzae, Yersinia enterocolitica, Yersinia pestis, Branhamella catarrhalis, Escherichia coli, Klebsiella pneumonia, Vibrio cholerae, Proteus mirabilis, Pseudomonas aeruginosa, Serrtia marcescens, Neisseria meningtidis, Salmonella typhimurium, Salmonella typhi, Salmonella paratyphi B, Mycobacterium tyberculosis, Chlamydia trachomatis,* Shigella spp., *Staphylococcus aureus, Pseudomonas aeruginosa,* Clostridium spp., *Escherichia coli, Yersinia pestis, Vibrio cholerae, Bordetella pertussis, Streptococcus pyogenes* bacterium, Streptococcus *mutans,* Plasmodium spp., Toxoplasma spp., *Leishmania* spp., *Schistosoma* spp., *Trypanosoma* spp., *Mycoplasma pneumoniae, Mycoplasma hominis,* and Streptococcus spp.

Viral agents include retroviruses (HTLV-I, HTLV-II, HIV-1, HIV-2, feline leukemia virus), myxoviruses (influenza A H1-H12, influenza B, influenza C); paramyxoviruses (parainfluenze 1-4, Newcastle disease virus, measles virus, respiratory syncytial virus, parotitis virus, distemper virus); hepatitis A virus, human rhinoviruses 1-113; rota viruses; herpes viruses (HSV 1, 2, cytomegalovirus, Epstein-Barr virus, equine abortion virus); papova viruses (BK virus, human wart virus); parvo viruses (mink enteritis virus, bovine parvo virus, feline parvo virus, procine parvo virus); human hepatitis B virus; Ebola and Marburg viruses; and hexone, pentone and fiber proteins of adeno viruses (human adeno viruses 1-33).

In the examples that follow, numbers have been assigned to fragments, compounds and analogs for ease in referring to them in the text. These fragments, compounds, and analogs are as follows:

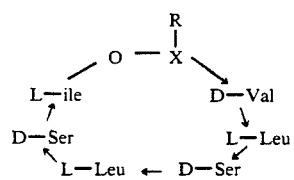

1: X = D—allo—Thr; R = D-3-Hydroxydecanoyl-L—Leu—D—Glu
2: X = D—Thr; R = D-3-Hydroxydecanoyl-L—Leu—D—Glu
3: X = D—allo—Thr; R = Decanoyl—L—Leu—D—Glu
4: X = D—allo—Thr; R = Octadecanoyl D-3-Hydroxydecanoyl-L—Leu—D—Glu—X—D—Val—L—Leu—D—Ser—L—Leu—D—Ser—L—ile—OH 5: X = D—allo—Thr
6: X = D—Thr D-3-Hydroxydecanoyl-L—Leu—D—Glu—NH$_2$

7

$$C_{14}H_{29}-\underset{\underset{CO_2H}{|}}{CH}-CH_2-CH_2-COBzl$$

8

$$C_{14}H_{29}-\underset{\underset{CO_2H}{|}}{CH}-CH_2-CH_2-CO_2H$$

9

10: R = D-3-Hydroxydecanoyl-L—Leu—OBzl—D—Glu—NH
11: R = D-3-Hydroxydecanoyl-L—Leu—D—Glu—NH
12: R = Decanoyl-L—Leu—OBzl—D—Glu—NH
13: R = Decanoyl-L—Leu—D—Glu—NH
14: R = C$_{14}$H$_{29}$—CH—CH$_2$—CH$_2$—COBzl
              |
              CO—NH
15: R = C$_{13}$H$_{27}$—CH—CH$_2$—CH$_2$—CO$_2$H
              |
              CO—NH
16: R = AcNH

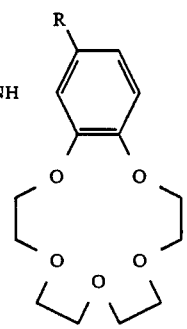

D-Hydroxydecanoyl-L—Leu—Gly—L—Ser—D—Val—L—Thr—L—Leu—OH

-continued

17

D-3-Hydroxydecanoyl-

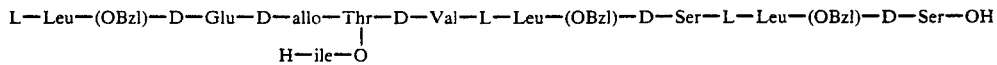
L—Leu—(OBzl)—D—Glu—D—allo—Thr—D—Val—L—Leu—(OBzl)—D—Ser—L—Leu—(OBzl)—D—Ser—OH
                              |
                         H—Ile—O

18

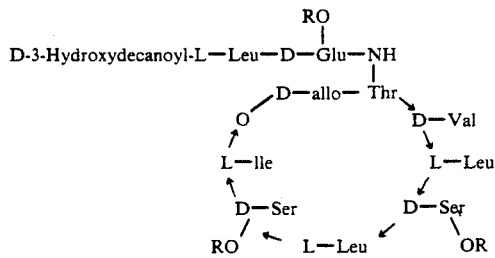

R = Bzl

19

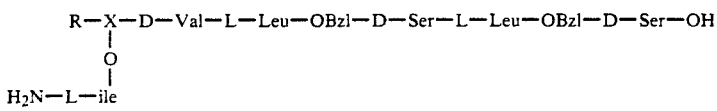
R—X—D—Val—L—Leu—OBzl—D—Ser—L—Leu—OBzl—D—Ser—OH
    |
    O
    |
H₂N—L—ile 20  X = D—Thr;      R = D-3-Hydroxydecanoyl-L—Leu—D—Glu
21  X = D—allo—Thr; R = Decanoyl-L—Leu—D—Glu
22  X = D—allo—Thr; R = Octadecanoyl 23  (±)-3-hydroxydecanoic acid
24  pentafluorophenyl D-3-hydroxydecanoate
25  D—allo—Thr
26  Fmoc—D—allo—Thr
27  Fmoc—D—allo—Thr—Pfp
28  alkoxybenzyl alcohol 1
29  Fmoc—D—Thr—Pfp

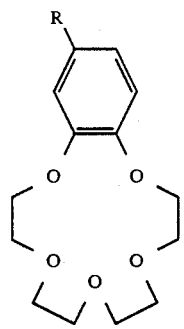

30  R = NO₂
31  R = NH₂
32  R = Boc—OBzl—D—Glu—NH
33  R = Boc—L—Leu—OBzl—D—Glu—NH

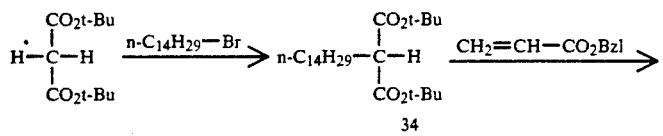

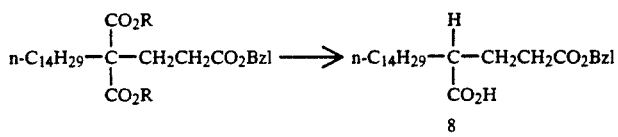

35  R = Bzl
36  R = H

EXAMPLE 1

Solid-Phase Synthesis of Viscosin, a Cyclic Depsipeptide with Antibacterial and Antiviral Properties Viscosin, a cyclic depsipeptide (containing a peptide lactone) was prepared by solid-phase chemistry using an Fmoc-protocol starting with an acid-sensitive resin. Cyclization with the activating agent BOP-Cl gave a product which was indistinguishable from natural viscosin, thereby supporting the proposed structure.

During the screening the microorganisms for antibiotic substances by Kochi at the Yokohama Medical College, it was found that an isolate from a culture of *Psuedomonas viscosa* had both antiviral[1] and antimicrobial activity against various mycobacteria.[2] The purified active substance was given the name viscosin. Structure (17) was proposed from the initial examination of viscosin which showed it to be a monocarboxylic peptide containing the fatty acid (−)-D-3-hydroxydecanoic acid.[3]

The fact that this structure was incorrect was shown by comparison of natural material with the synthetic structure (1) obtained by solution synthesis.[4] The revised structure (1) was proposed based on further physical characterization which indicated viscosin to be a cyclic depsipeptide (a peptide lactone) having alternating D and L-amino acids with an N-terminal D-3-hydroxydecanoyl group.[5] Ring closure is through an ester linkage between the carboxyl of L-Ile and the hydroxyl of D-allo-Thr, leaving the gamma-carboxyl of D-Glu free. To further strengthen the structural assignment, work was undertaken to prepare (1) by a scheme which utilized solid-phase techniques.

The central problem in the synthesis of cyclic depsipeptides is ring closure. It has been found that ring closure is most advantageously effected through amide bond formation rather than through ester formation, and there are numerous examples of such cyclization.[6] One problem with the use of solid-phase synthesis in the preparation of cyclic depsipeptides has been the difficulty of maintaining full side-chain protection in the linear precursor during HF resin cleavage. In an effort to use recent technique of solid-phase synthesis for the preparation of cyclic depsipeptides, a scheme was developed to employ these techniques in the synthesis of viscosin. Examination of viscosin shows that linear precursor 18 (see below) would be a suitable target for preparation by solid-phase synthesis as cyclization to the desired benzyl-protected viscosin 19 would result from amide bond formation between the C-terminal carboxyl of OBzl-D-Ser and the amino group of L-Ile. To prepare 18 by solid-phase synthesis and preserve the benzyl protecting groups during cleavage from the resin, a synthetic scheme was employed using fluorenylmethoxycarbonyl (Fmoc) protected amino acids[7] and the acid-sensitive alkoxybenzyl alcohol resin of Wang[8] (which can be cleaved with 50% trifluoroacetic acid (TFA) in $CH_2Cl_2$). The choice of Boc-amino protection for Ile relies on its stability to the conditions of Fmoc deprotection during peptide synthesis. However, treatment of the resin with TFA would simultaneously remove the Boc group and cleave the peptide from the resin, yielding fragment 18 directly with both amino and carboxyl ends deprotected for cyclization. The value of simultaneous deprotection of amino and carboxyl terminal groups leading directly to material suitable for cyclization has been shown recently in solution synthesis.[9]

Coupling of amino acids through D-Val followed a standard Fmoc-based protocol. In summary, Fmoc-OBzl-D-Ser (all Fmoc-amino acids were either purchased or synthesized as crystalline solids using Fmoc-N-hydroxysuccinimide ester[10]) was coupled to alkoxybenzyl alcohol resin (1.0 mmol —OH $g^{-1}$ resin) using dicyclohexylcarbodiimide (DDC) activation in the presence of 0.1 eq. of dimethylaminopyridine (DMAP)[11], to yield 0.4 to 0.6 mmol/g resin. After capping the resin with benzoyl chloride[8], the synthesis was continued through Fmoc-D-Val using the following repetitive protocol for sequential coupling of Fmoc-amino acids to the growing peptide chain: (1) 3×DMF washes, (2) 3×$CH_2Cl_2$ washes, (3) amine deprotection using piperidine: DMF, 1:1, 20 min, (structure 4) coupling amino acid using 2.5 eq of Fmoc amino acid, hydroxybenzotriazole (HOBT)[12] and DCC in DMF, 2–3 h, (structure 5) monitoring of coupling using the Kaiser ninhydrin test[13], repeating the coupling if not completed. Single couplings were adequate for Fmoc-OBzl-D-Ser and Fmoc-D-Val, with multiple couplings being required for Fmoc-L-Leu approximately 50% of the time.

One important aspect of the use of solid-phase chemistry in the synthesis of cyclic depsipeptides is the preparation of the ester branch point while the peptide is still attached to the resin. In this regard, the strategy for building the Boc-L-Ile ester branch point called for the addition of Fmoc-D-allo-Thr with its side chain hydroxyl unprotected. Although such coupling of an unprotected Thr is known in solution synthesis, it has been assumed that this was incompatible with solid-phase synthesis due to self-acylation resulting from the large excess of amino acid needed to achieve high coupling efficiency. Since direct DCC mediated coupling could result in significant acylation of the unprotected hydroxyl[14], coupling was achieved using the pentafluorophenyl ester (Pfp)[15], which reacts rapidly with amines, but sluggishly with alcohols. Although D-allo-Thr is not readily commercially available, epimerization of D-Thr gave an inexpensive source of D-allo-Thr.[16] This was first protected as the Fmoc derivative, then esterified with pentafluorophenol/DCC to yield Fmoc-D-allo-Thr-Pfp before coupling cleanly and quantitatively to the resin in a single coupling reaction using 2.5 eq. of amino acid, 5 h in DMF. As anticipated, examination of a sample of TFA-cleaved resin by HPLC gave no indication of significant acylation of the D-allo-Thr hydroxyl.

It was anticipated that esterification of the Fmoc-D-allo-Thr hydroxyl with Boc-L-Ile directly could lead to side-product formation due to O→N shift of Boc-Ile under the conditions which would subsequently be necessary to deblock the Fmoc-D-allo-Thr.[17,18] Since the reverse, N→O shift would not be expected to occur under the non-acidic conditions of the synthesis, the resin was first deblocked with piperidine in the usual manner and then coupled with Fmoc-OBzl-D-Glu-Pfp. Again, the use of Pfp activation allowed amino coupling to occur without acylation of the unprotected hydroxyl. The free hydroxyl of D-allo-Thr was then esterified with Boc-L-Ile/DCC activation (with 0.1 eq. of DMAP[19]) to give the desired Fmoc-OBzl-D-Glu-(O-Boc-L-Ile)-D-allo-Thr branch point as a single major product on HPLC.

Having successfully prepared the branch pint, it was then found that piperidine deblock of the Fmoc-OBzl-D-Glu followed by coupling with Fmoc-L-Leu (DCC/HOBT) gave a major side product which was at times equal to 40% of the desired product. This chain-terminated side product gave amino acid analysis and fast atom bombardment (FAB) mass spectral data consistent with the cyclization[20] of the OBzl-D-Glu to pyroglutamic acid. This was readily removed chromatographically and in subsequent synthesis was essentially eliminated by decreasing the piperidine deblock time to 5 min.

Linear peptide (18) was completed by acylating the peptide resin with the Pfp-ester of D-3-hydroxydecanoic acid in DMF. Again, the use of Pfp ester activation allowed the acid to be coupled with its hydroxyl unprotected. 3-Hydroxydecanoic acid (mp 55°–56° C., 57° C.)[21] was synthesized from n-octyl aldehyde by reaction with lithium tert-butyl acetate[22] followed by TFA hydrolysis and resolution as the (−)-cinchonidine salt (mp 119°–120° C., 119°–120° C.) which upon neutralization gave (−)-D-3-hydroxydecanoic acid ($[\alpha]_D = -21.4°$ C. (c 1.0, CHCl$_3$); lit. $[\alpha]D = -17.5°$).[19] The final peptide was cleaved from the resin with TFA (50% in CH$_2$Cl$_2$, 30 min) and lyophilized from dioxane to yield the crude peptide (18). This was readily purified by reverse phase HPLC using a C$_{18}$ column and an H$_2$O-acetonitrile gradient system containing 0.1% TFA, with the resulting peptide being relyophilized from dilute anhydrous dioxane —HCl to yield (18).HCl as a white solid in 25% overall yield based on resin substitution.

To complete the synthesis, cyclization reactions were carried out with a peptide concentration of 1 mM. Using DCC/HOBT in the presence of triethylamine, a single main product was obtained having a FAB mass spectrum consistent with the N-acylurea resulting from the O←→N peptide rearrangement of the intermediate O-acylisourea[24] formed by reaction with DCC. Using bis(2-oxo-3-oxazolidinyl)phosphinic chloride (BOP-Cl)[25] and triethylamine in dioxane, the desired cyclic (19) (amino acid analysis, FAB mass spectrum) was obtained in 24% yield from 18 after HPLC purification. Debenzylation was carried out in MeOH using ammonium formate and 10% Pd-C.[26] Purification of the crude reaction product by HPLC yielded a white solid in 78% yield which had the expected amino acid analysis and FAB mass spectrum consistent with (1). Synthetic (1) was shown to be identical to natural viscosin both chromatographically (HPLC using a reverse-phase C$_{18}$ column with an aqueous acetonitrile system containing 0.1% TFA) and by NMR (300 MHz proton spectrum) thereby supporting (1) as the correct structural assignment for viscosin.

In summary, the successful synthesis of cyclic depsipeptides by solid-phase techniques is possible through the preparation of suitable branched fragments. Important aspects of this approach are the use of orthogonal Fmoc/Boc amino protection. Elaboration of the crucial ester branch point using unprotected hydroxyl-bearing amino acids is possible through the use of Pfp activiation and a coupling order which minimizes O←→N acyl migration.

EXAMPLE 2

Methodology developed in the synthesis of viscosin was used to prepare analogs of viscosin designed to explore specific features of the molecule as they relate to antitrypanosomal activity. The results of this latter structure-activity study are described below.

SYNTHESIS

Peptide Lactones

In the preparation of peptide lactones ring closure is most advantageously effected through amide bond formation rather than through esterification.[27] The linear depsipeptide fragments required for cyclization are usually synthesized by solution methods,[28] but solid-phase techniques have also been applied to the synthesis of these molecules.[29,30] The development of acid-sensitive resins which can be cleaved with trifluoracetic acid (TFA),[8] acid-stable fluorenylmethyloxycarbonyl (Fmoc) amino protection[31] and pentafluorophenol (Pfp) active ester coupling[15,32] provided the basis for the solid-phase synthesis of viscosin. A key feature of the viscosin synthesis was its reliance on the preferential reactivity of Pfp esters with amines in the presence of alcohols,[33] for coupling of amino acids without hydroxyl group protection. In this manner the benzyl protected linear fragment (18) was prepared by solid-phase techniques with the Ile ester branch point preformed and suitable for direct cyclization.

The four peptide lactones (1–4) which required the solid-phase synthesis of the corresponding linear fragments 18, 20–22 were prepared using alkoxybenzyl alcohol resin[8] in a manner similar to that described above for the synthesis of viscosin. Coupling through Fmoc-D-Val was the same for each analog, using hydroxybenzotriazole (HOBT)/dicyclohexylcarbodiimide (DCC)[10] mediated coupling of Fmoc-protected amino acids (either obtained commercially or synthesized as crystalline solids using 9-fluorenylmethyloxysuccinimidly carbonate (Fmoc-OSu)[34]). Epimerization of D-Thr (25) provided a ready source of D-allo-Thr ($[\alpha]_D = -32.7°$; $[\alpha]_D 2 = -33.2°$).[35] Although coupling of hydroxyl-bearing amino acids such as Thr and Ser are conducted without hydroxyl protecting in solution synthesis where large excesses of amino acid are not required,[27,36] side chain acylation has been reported for such reactions during solid-phase synthesis.[37] Relying on the selective reactivity of Pfp esters towards amines in the presence of alcohols,[33] it was possible to safely couple amino acids with unprotected hydroxyls both on the incoming amino acid and on the resin. Synthesis of Fmoc-D-allo-Thr (26) and Fmoc-D-Thr were as described for the synthesis of Fmoc-L-Thr[10] with conversion to the corresponding Pfp esters by reaction with pentafluorophenol in the presence of DCC. (Synthesis of Fmoc-Thr-Pfp is possible directly from Thr by reaction wit 9-fluorenylmethyl pentafluorophenyl carbonate[38]). Solid-phase coupling of both Fmoc-D-allo-Thr-Pfp (27) and Fmoc-D-Thr-Pfp (29) was achieved using 1.5 equivalents with reaction completion indicated by the Kaiser ninhydrin test.[33]

At this stage it is possible to construct the Boc-L-Ile branch point by esterifying the unprotected hydroxyl of either Fmoc-D-allo-Thr (for peptides 18, 21 and 22) or Fmoc-D-Thr (analog 20). However, this could result in significant side product formation during the subsequent piperidine catalyzed deblock of the Fmoc group due to an O→N migration of Boc-L-Ile.[17,18] Since the reverse N→O migrations do not readily occur under the nonacidic conditions of the synthesis, the problem of acyl migration can be circumvented by initial acylation of nitrogen with subsequent esterification of the hydroxyl. Use of Pfp ester activation allowed this amidation to proceed in the presence of the unprotected hydroxyl. Therefore, the Fmoc-D-allo-Thr[40] was deblocked with piperidine and the resulting nitrogen acylated with the appropriate Pfp ester (Fmoc-OBzl-D-Glu-Pfp for peptides 18 and 21; octadecanoyl-Pfp for 22). The remaining free hydroxyl of D-allo-Thr[40] was then esterified with Boc-L-Ile using DCC in the presence of 0.1 equivalents of dimethylamino pyridine (DMAP).[19]

Synthesis of analogs 18, 20, 21 proceeded by a shortened piperidine deblock of Fmoc-OBzl-D-Glu.[41] The reduction of deblock from 20 to 5 minutes was necessary to prevent the cyclization[20] of OBzl-D-Glu to pyroglutamic acid. The orthoganol Boc/Fmoc protection scheme allowed the selective removal of the base labile Fmoc group, while maintaining the base insensitive Boc protection on the L-Ile. The synthesis was continued by coupling of Fmoc-L-Leu[42] in the usual manner (DCC/HOBT) which was followed by piperidine-catalyzed Fmoc deprotection (20 minutes) and final acylation with either (−)-D-3-hydroxydecanoic acid (−) (23) (for peptides 18 and 20) or decanoic acid (for analog 21). Coupling of D-3-hydroxydecanoic acid was as the Pfp ester (24), with the 3-hydroxyl group unprotected. The acid was obtained by (−)-cinchonidine resolution[21] of synthetic (±)-3-hydroxydecanoic acid [(±) 12]. The (±)-3-hydroxydecanoic acid itself (mp 55°–56° C.; 57° C.) was synthesized by the aldol condensation of lithium tert butyl acetate[22] with n-octyl aldehyde, followed by TFA hydrolysis of the resulting (±)-tert butyl acetyl-3-hydroxydecanoic acid.

Treatment of the resulting resins with 50% TFA in $CH_2Cl_2$ (30 minutes) resulted in simultaneous cleavage of the peptides from the support and removal of the Boc amino protection. The crude linear peptides 18, 20–22 were purified by preparative high-pressure liquid chromatography (HPLC) and converted to HCl salts. Cyclizations were carried out in 1 mM dioxane solutions using bis(2-oxo-3-oxazolidinyl)phosphinic chloride (BOPCl)[25,39] in the presence of triethylamine, giving crude benzyl protected cyclic peptides. The crude peptides were debenzylated directly using ammonium formate and 10% Pd.C[26] in methanol (55°–60° C., 3 hr), giving after HPLC purification, the finished peptide lactones 1–4. Experience in the synthesis of viscosin had indicated that HPLC purification of intermediate benzyl protected peptide lactones prior to debenzylation did not increase either the yield or quality of the final debenzylated peptide, and therefore it was deemed advantageous to omit this purification step. Preparative HPLC of peptides in this work was carried out on a scale of up to several hundred milligrams utilizing a 4.7×30 cm radial compression cartridge with $C_{18}$ packing and acetonitrile-$H_2O$ solvent system containing 0.1% TFA. The desired fractions could safety be taken to dryness using rotary evaporation at temperatures up to 60° C. without significant decomposition.

Linear Fragments

Synthesis of viscosic acid 5 and [D-Thr]-viscosic acid 6 utilized acid-sensitive alkoxybenzyl alcohol resin and Fmoc-chemistry in a manner similar to that used to make the linear fragments 18, 20–22. Fmoc-L-Ile-alkoxybenzyl alcohol resin used as starting material was either purchased commercially or synthesized by reaction of commercially available Fmoc-L-Ile with alkoxybenzyl alcohol resin in the presence of dimethylformamide dineopentyl acetal (RT, 3 days)[43] followed by capping with benzoyl chloride providing 0.37 mmol/g resin substitution. Coupling of all amino acids beyond D-Val was as their Pfp esters with D-allo-Thr (for 5), D-Thr (for 6) and D-β-hydroxydecanoic acid (for 5 and 6) having their hydroxyls unprotected. The finished resins were cleaved with 50% TFA in $CH_2Cl_2$, evaporated to dryness under rotary evaporation and lyophilized from dioxane to yield benzyl-protected peptides as white solids which were debenzylated in the usual manner (ammonium formate, 10% Pd-C/MeOH, 55°–60° C.) and purified by preparative HPLC.

Preparation of linear fragment 7 was by solid-phase techniques starting from 4-methylbenzhydrylamine resin.[44] This was coupled twice with 2.5 equivalents Fmoc-OBzl-D-Glu using DCC, HOBT (3 hr) giving a negative Kaiser reaction. The resin was then deblocked with 50% piperidine in DMF for 5 min, washed and coupled with 2.5 equivalents of Fmoc-L-Leu (DCC, HOBT). A final piperidine deblock was followed by coupling with the Pfp ester of D-β-hydroxydecanoic acid to yield the finished resin which was dried. The resin was cleaved with anhydrous hydrogen fluoride (45 min, 0° C.) in the presence of anisole, extracted, lyophilized and purified by preparative HPLC.

BIOLOGICAL

Discussion

That peptides can have dramatic effects on cell membranes is well-known. Cyclic peptides such as valinomycin,[45] the enniatins,[46] the polymixins,[47] and more recently EM 49[48] and the Echinocandins[49] are though to owe at least some of their antimicrobial activity to their ability to alter the integrity of cell membranes. Linear molecules can also cause lysis of cell membranes. Protein-size molecules such as diphtheria toxin[50] and cytolytic complement complexes[51] exert their lytic effects through association into transmembrane pores. This pre-forming mechanism is also an apparent explanation for small linear peptides such as the cercropins (from the humoral defense system of the giant silk moth *Hyalophora cecropia*)[52] and the maganinis[53] (also known as PGS[54]) which are thought to form transmembrane α-helixes. Peptides studied to date as antichagaisic agents also apparently relay on membrane-active mechanisms[55,56] (an exception being fibronectin fragment analogs which interfere with *T. cruzi* attachment to host cell membranes[57]).

Because *T. cruzi* is a unicellular organism whose life cycle intimately depends on the interaction of its plasma membrane with host structures, it might be expected that the membrane is highly developed and selective in its actions. Studies conducted on the membrane composition of *T. cruzi* have shown that the fatty acid composition is unique, ranging up to 22 carbons with linoleic acid (Δ-$C_{18}$) being the major fatty acid, even though other fatty acids may predominate in the extracellular medium.[58] There is a requirement for stearic ($C_{18}$) acid when grown in defined media,[59] and while fatty acids of chain length 12 and 16 carbons are toxic to *T. cruzi*, the 18 carbon linoleic acid is not toxic even in molar concentrations. It is also known that long-chain fatty acids are extremely toxic to other trypanosomes, with toxicity varying widely among closely related fatty acids.[60,61] A lytic effect against *T. cruzi* has been observed in a long-chain fatty acid fraction from the marine alga *Ulva lactuca*,[60] and cod-liver oil, which is enriched in long-chain fatty acids, has been shown to have a suppressive effect on some trypanosome infections in mice.[62]

As seen with antitrpanosomal factors derived from *Pseudomonas fluorescens*,[55] the most readily apparent effect of viscosin on *T. cruzi* is to cause disruption of the cell membrane. It can be speculated that viscosin is acting as either a cell-specific detergent or as an ionophore, a property of other cyclic peptides.[63] Viscosin along with a number of other cyclic peptide antibiotics has a fatty acyl portion,[64] and the fatty acid portions of antibiotics such as EM49 and the polymyxins have been shown to be extremely important to their activity perhaps by aiding in insertion of the molecules into the lipid membranes.[65] Since *T. cruzi* is quite specific as to the fatty acids it will incorporate,[66] it may be possible to utilize this specificity as a means of increasing selectivity and toxicity of peptide analogs towards *T. cruzi*.

Since there has been no structure-activity work reported on the efficacy of viscosin towards trypanosomes such as *T. cruzi*, a series of analogs were synthesized in an effort to increase specificity and toxicity towards *T. cruzi* and to decrease the synthetic complexity. Therefore, analogs 3 and 2 were prepared respectively with the D-$\beta$-hydroxydecanoic acid replaced by the simpler decanoic acid and the D-allo-Thr replaced by the more readily available D-Thr. Analog 4, which replaces the D-$\beta$-hydroxydecanoyl-L-Leu-D-Glu side chain with a simple $C_{18}$ amide, was designed to increase affinity and uptake by *T. cruzi* by taking advantage of the unique role $C_{18}$ acids apparently occupy in the *T. cruzi* membrane. In principle, this analog relies on the side chain to direct and anchor the peptide in the trypanosome membrane, with lytic activity residing potentially in the peptide ring. It should be noted that in viscosin itself the chain length from the $\gamma$-carboxyl of D-Glu to the end of the acyl side chain is 18 units. The possibility exists, however, that antibiotic activity of viscosin resides principally in the side chain, and not in the ring. Such antibiotic activity has been observed in other small fatty acylated mon- and dipeptides.[67, 68] Therefore, side chain fragment 7 was prepared to examine this possibility. Finally, linear analogs, viscosic acid 5 and [D-Thr[7]]-viscosic acid 6 were prepared to examine the activity of ring-opened derivatives.

Experimental Section

Melting points were determined on a MelTemp melting point apparatus and are uncorrected. Fast atom bombardment mass spectra (FAB MS) and chemical ionization mass spectra (CIMS) were determined either at Oneida Research Services, Inc. (Whitesbore, N.Y.), the Mass Spectrometry Facility of the University of Maryland Department of Chemistry (College Park, Md.), or at the Middle Atlantic Mass Spectrometry Laboratory (The Johns Hopkins University, Baltimore, Md.). Ultraviolet spectroscopy was performed on a Hewlett Packard Model 8451A spectrometer. Optical rotations were recorded on a Perkin-Elmer 241MC polarimeter. High pressure liquid chromatography (HPLC) was performed using a Waters Division of Millipore LC 3000 solvent delivery system equipped with a Rheodyne 7010 injector, a Model 381 variable wavelength detector, a Model 740 data module, and for preparative work , either a PrepPak 1000 radial compression module equipped with a Bondapak $C_{18}$ 4.7×30 cm (15–20μ particle size) cartridge (run at 60 mL/min) or a YMC $C_{18}$ column (10μ particle size, 120 Å pore; 20 mm×250 mm) run at 20 mL/min. Flash chromatography was performed using EM Kieselgel 60, 230–400 mesh. Substitution of alkoxybenzyl alcohol resins was by UV absorbance at 267 nm ($\epsilon$=18,950[69]) following cleavage with 50% trifluoroacetic acid (30 min). Combustion analysis was performed at Galbraith Laboratories, Inc. (Knoxville, Tn.) and were within 0.4% of theoretical values unless otherwise indicated.

SYNTHESIS

(±)-3-Hydroxydecanoic acid [(±)-23]

A solution of lithium diisopropylamide was prepared by diluting 125 mL (200 mmol) of 1.6M n-butyl lithium in hexane with 300 mL of toluene, and stirring with 20.2 g (200 mmol) of diisopropylamine for 30 min at 0° C. This was cooled to −78° C., stirred with 23.2 g (200 mmol) of tert-butyl acetate (1 hr), then at 0° C. (1 hr). A total of 20.5 g (160 mmol) of octyl aldehyde was added, then the reaction was brought to RT and stirred 1 hr. The reaction was quenched by addition of 10% HCl and solvent removed by rotary evaporation under reduced pressure. The resulting yellow oil was treated with neat TFA (150 mL, 30 min, RT), then evaporated to dryness and partitioned between dilute aqueous HCl and $CH_2Cl_2$. The combined organic phase was washed with saturated NaCl, dried ($MgSO_4$) and taken to dryness by rotary evaporation. Crystallization of the resulting reddish oil from hexane yielded (±)-12 as white crystals (20.0 g, 67% yield), mp 55°–57° C. (lit. 57° C.). CIMS ($NH_3$): m/z 206 ($M+NH_4^+$).

(−)-D-3-Hydroxydecanoic acid[(−)-23]

(±)-3-Hydroxydecanoic acid 12 20.0 g (106 mmol) was resolved as the (−)-cinchonidine salt following literature procedures.[21] After seven crystallizations from $CCl_4$ and two from ethyl acetate (all crystallizations were carried out at RT), a total of 6.2 g of (−)-cinchonidine.(−)-3-hydroxydecanoate salt was obtained, mp 121°–122° C. (mp 119°–120° C.). The salt was partitioned between 0.5N HCl (100 mL) and $CH_2Cl_2$ (3×100 mL) and the combined organic layers were washed with saturated NaCl (2×100 mL), dried ($MgSo_4$) and evaporated to an oil which crystallized. Recrystallization from hexane yielded (−)-23 as white crystals (2.3 g 23%), mp 46°–47° C., $[\alpha]_D$=−21.4° (c 1.0, $CHCl_3$) (mp 47° C., $[\alpha]_D$=17.5° (c 0.9, $CHCl_3$)).

Pentafluorophenyl D-3-hydroxydecanoate (24)

A solution of (−)-3-hydroxydecanoic acid (−)-23 (3.76 g, 20 mmol, pentafluorophenol (4.04 g, 22 mmol) and dicyclohexylcarbodiimide (4.32 g. 21 mmol) in $CH_2Cl_2$ was stirred at RT for 3 hr. The mixture was then cooled in ice, dicyclohexylurea was removed by filtration and the filtrate evaporated to a colorless oil. Purification by silica gel flash chromatography (5 cm dia×25 cm column, $CH_2Cl_2$) yielded product 24 as a colorless oil which crystallized (6.50 g, 92%) mp 48°–49° C. CIMS ($NH_3$); m/z 372 ($M+NH_4^+$). Anal. ($C_{16}H_9F_5O_3$) C, H.

D-allo-Thr (25)

Synthesis of D-allo-Thr 25 was by literature procedures[16] starting from D-Thr.(54% overall yield, $[\alpha]_D$=−32.7° (c1.0, 1N HCl); and $[\alpha]_D$=−33.2° (c 1.0, 1N HCl)).[35]

Preparation of Fmoc Amino Acids

All Fmoc amino acids were synthesized from the corresponding free amino acids by the following general procedure: To a solution of D-allo-Thr (25) (1.62 g, 13.6 mmol) and $NaHCO_3$ (3.4 g, 41 mmol) in $H_2O$ (60 mL) was added a solution of Fmoc-OSu (4.58 g 13.6 mmol) in dioxane (60 mL) and the turbid reaction mixture stirred at RT overnight. The mixture was then diluted with $H_2O$, acidified to pH$\leq$4 by addition of 37% HCl and extracted with ethyl acetate (3$\times$100 mL). The combined ethyl acetate extracts were washed with saturated NaCl (2$\times$100 mL), dried ($MgSO_4$) and taken to dryness by rotary evaporation to give a colorless oil which was crystallized from ethyl acetate/hexane, yielding Fmoc-D-allo-Thr (26) as white crystals (3.7 g, 80%), mp 152°–153° C. Anal. ($C_{19}H_{19}NO_5$) C, H, N.

Preparation of Pfp esters of Fmoc protected amino acids

The following is a typical procedure used to prepare Pfp esters of Fmoc protected amino acids: to a solution of Fmoc-D-allo-Thr (26) (3.41 g, 10.0 mol) and pentafluorophenol (2.29 g, 12.0 mmol) in dioxane (40 mL) was added a solution of DCC (2.06 g, 10.0 mmol) in dioxane (10 mL) and the reaction stirred at RT overnight. The mixture was then cooled in ice, dicyclohexyl urea removed by filtration, and the filtrate evaporated to a colorless oil which crystallized. Trituration with hexane yielded product (27) as 5.00 g (100%) of white solid, mp 142°–144° C. Anal. ($C_{25}H_{18}F_5NO_5$) C, H, N.

Synthesis of Fmoc-D-Val-L-Leu-OBzl-D-Ser-L-Leu-OBzl-D-Ser-alkoxybenzyl alcohol resin (28)

Solid-phase synthesis employed manual techniques using apparatus as previously described.[70] Mixing of resin was by a rocking motion of 28 cycles per min with solvent used in the proportion of 5 mL/g resin. Starting alkoxybenzyl alcohol resin 10.0 g (0.65 mmol-OH/g resin; either synthesized from choromethyl resin[8] or purchased from commercial sources) was washed with DMF (4$\times$), $CH_2Cl_2$ (4$\times$) then coupled with Fmoc-OBzl-D-Ser 19 (6.78 g, 16.5 mmol), DCC (3.35 g, 16.25 mmol), pyridine (1.28 g, 16.25 mmol) and dimethylamino pyridine (0.08 g, 0.65 mmol) in 50 mL DMF (3 h), giving a resin substitution of 0.36 mmol/g. The coupling was repeated identically resulting in a substitution of 0.66 mmol/g. The resin was washed with DMF and $CH_2Cl_2$ (3$\times$ each) then capped by treating with benzoyl chloride (0.40 g, 10 mmol) and pyridine (790 mg, 10 mmol) in 50 mL $CH_2Cl_2$ (30 min.). Coupling cycles were then begun as follows: The resin was washed with DMF (3$\times$); $CH_2Cl_2$ (3$\times$); deblocked with 50% piperidine in DMF (50 mL, 20 min.); washed with DMF (3$\times$) and $CH_2Cl_2$(3$\times$) then coupled with 2.5 equivalents each of Fmoc amino, DCC and HOBT in 50 mL DMF. After 3 h the resin was monitored for unreacted amino groups by the Kaiser test.[13] If necessary, coupling was repeated in an identical manner to achieve a negative Kaiser reaction. Following completion of the coupling process, the resin was washed, deblocked and coupled with the next amino acid as indicated above. The results of several synthesis indicated that while single couples were usually adequate for Fmoc-OBzl-D-Ser and Fmoc-D-Val, multiple couples were required for Fmoc-L-Leu approximately 50% of the time. Coupling was continued through Fmoc-D-Val, then the resin was removed, dried and portions used for further elaboration as indicated below.

Viscosin Linear Fragment (18)

A total of 4 g (3 mmol) of resin 28 was washed with DMF (3$\times$20 mL), deblocked (20 mL of 50% piperidine in DMF, 20 min.), washed (6$\times$20 mL DMF) and reacted with 1.5 equivalents (1.52 g, 3 mmol) of Fmoc-D-allo-Thr-Pfp ester (27) in 20 mL DMF. Following completion of coupling (1.5 h as indicated by a negative Kaiser test), the resin was washed with DMF and $CH_2Cl_2$ (3$\times$20 mL each), deblocked with piperidine as before and coupled to completion with 1.5 equivalents of Fmoc-OBzl-D-Glu-Pfp ester (1.88 g, 3 mmol) in 20 mL DMF (1.5 h). The resin was then washed (3$\times$10 mL each DMF, $CH_2Cl_2$) and esterified directly by coupling twice (2 h per couple) with 2.5 equivalents Boc-L-Ile (1.16 g, 5.0 mmol), DCC (1.03 g, 5.0 mmol), pyridine (395 mg, 5.0 mmol) and DMAP (61 mg, 0.5 mmol) in DMF (20 mL). (NOTE: There is no piperidine deblock before this esterification.) The resin was washed and subjected to an abbreviated piperidine deblock (50% piperidine in DMF, 5 min.) before coupling with 5 equivalents of Fmoc-L-Leu (2.31 g, 10 mmol) and DCC (2.06 g, 10 mmol). Coupling was complete after 3 h and the resin was washed, deblocked as previously described with piperidine (5 min.) and reacted with D-3-hydroxydecanoic acid-Pfp ester 24 (750 mg, 2.1 mmol) in 10 mL of $CH_2Cl_2$ (4 h). The finished resin was cleaved with 50% TFA in $CH_2Cl_2$ (20 mL, 30 min.) and the product evaporated to dryness and lyophilized from dioxane to yield 1.2 g crude 5. Purification by preparative HPLC was conducted in two batches (PrepPak 1000 radial compression cartridge; 0.1% TFA in an acetonitrile: $H_2O$ system run at 60 mL/min. in a linear gradient from 0→70% acetonitrile over 60 min.) yielding after lyophilization purified (18) as a white solid (740 mg, 26% yield based on resin substitution). FAB MS m/z:1414(M+1).

[D-Thr[6]]-Viscosin Linear Fragment (20)

Synthesis of 20 was accomplished in a manner similar to that used to prepare linear viscosin fragment 18, except that Fmoc-D-Thr-Pfp (29) was used rather then Fmoc-D-allo-Thr-Pfp (27). Starting with 0.8 mmol of rein 28, 635 mg of crude peptide was obtained, which yielded 139 mg (12% yield based on resin substitution) of purified 20 following HPLC purification as indicated for 18. FAB MS m/z: 1415 (M+1); 1453 (M+ K+).

Deshydroxy-Viscosin Linear Fragment (22)

Synthesis of 21 was accomplished in a manner similar to that used to prepare linear viscosin fragment 18, except that pentafluoro decanoate was used rather than pentafluoro D-3-hydroxydecanoate. A 1 mmol synthesis produced 535 mg (38%) of purified 21 following preparative HPLC as indicated for 21. FAB MS m/z: 1398 (M+1).

Octadecanoyl Linear Fragment (22)

Synthesis of 22 on a 1 mmol scale was accomplished in a manner similar to that used to prepare linear viscosin fragment 18 through the coupling of Fmoc-D-allo-Thr. At this point the resin was deblocked with piperidine and washed in the usual manner. A mixture of stearic acid (568 mg. 2.0 mmol), pentafluorophenol (442 mg, 2.4 mmol) and DCC (412 mg, 2.0 mmol) in $CH_2Cl_2$ (20 mL) was stirred at RT for 30 min., then added to the deblocked resin. After 3 h the reaction had failed to go to completion as indicated by a Kaiser test. Recoupling with 550 mg (1.0 mmol) of stearic anhydride in $CH_2Cl_2$ (20 mL) in the presence of triethylamine (200 mg, 2 mmol) gave a negative Kaiser test after 20 min. The resin was washed and coupled twice (3 h each) with 1.15 g (5 mmol) of Boc-L-Ile 1.03 g (5 mmol) of DCC, 63 mg (0.5 mmol) of DMAP and 400 mg (5 mmol) of pyridine in DMF (20 mL). The resulting resin was cleaved with 50% TFA in $CH_2Cl_2$ (30 min.) and lyophilized from dioxane as previously indicated. Preparative HPLC (PrepPak 1000 cartridge system) of the resulting crude peptide was performed. A total of 840 mg (71%) of purified (22) was obtained as a white solid. FAB MS m/z: 1179 (M+1), 1201 (M+Na$^+$), 1224 (M+2Na$^+$).

Viscosin (1)

A total of 200 mg (140 μmol) of linear 18 was dissolved in 20 mL of dry dioxane (4 Å sieves), 20 dps of 4N.HCl dioxane was added and the solution taken to dryness under rotary evaporation (40° C.). The process was repeated, giving a residue which was derived under high vacuum. This was suspended in dry dioxane (140 mL) and stirred with 43 mg (168 μmol) BOPCl and 283 mg (2.8 mmol triethylamine (48 h)). The cloudy reaction mixture was taken to dryness by rotary evaporation (40° C.), then resuspended in methanol (50 mL) and stirred at 55° C. with 880 mg (14 mmol) ammonium formate and 300 mg 10% Pd.C (5 h). Removal of Pd.C by filtration and rotary evaporation of the filtrate gave crude viscosin as a colorless resin which was purified by preparative HPLC (PrepPak 1000 cartridge system). A total of 45 mg (29%) of purified 1 was obtained as a white solid. FAB MS m/z: 1126 (M+1), 1148 (M+Na$^+$), 1164 (M+K$^+$). Addition of CsCl produced a base peak of 1258 (M+Cs$^+$).

[D-Thr$^6$]-Viscosin (2)

Cyclization of 83 μmol of linear 20 was in a manner similar to that indicated for cyclization of linear viscosin fragment 18. After reacting with 1.2 equivalent of BOPCl for 24 h, an additional 1.2 equivalents of BOPCl was added and the cyclization continued for 44 h. The crude reaction mixture was evaporated to dryness, debenzylated as indicated for 1, and purified twice by preparative HPLC giving 10 mg (11% yield) of purified 2. FAB MS m/z: 1127 (M+1), 1149 (M+Na$^+$).

Deshydroxy Viscosin (3)

Cyclization and subsequent debenzylation of linear 21 was performed on a 150 μmol scale in a manner similar to that indicated for cyclization of linear viscosin fragment 18. The resulting crude peptide lactone was purified by preparative HPLC (PrepPak 1000 cartridge system). A total of 86 mg (52%) of purified 3 was obtained as a white solid. FAB MS m/z: 1110 (M+1), 1148 (M+K$^+$).

Octadecanoyl Viscosin (4)

Cyclization (24 h reaction time) and debenzylation of 300 μmol of linear 22 was performed as indicated for the preparation of viscosin 1. The crude product was purified twice by preparative HPLC using the PrepPak 1000 cartridge system giving 24 mg (10%) of purified 4 as a white solid. FAB MS m/z: 980 (M+1).

Viscosic Acid (5)

A total of 2.0 g of alkoxybenzyl alcohol resin (0.6 mmol —OH/g resin) was placed in a manual synthesis shaker and washed (3×10 mL DMF; 3×10 mL $CH_2Cl_2$) then shaken for 3 days with a solution of Fmoc-L-Ile (1.76 g, 5 mmol) and dimethylformamide dineopentyl acetal (1.15 g, 5 mmol) in $CH_2Cl_2$ (10 mL). The resin was then washed, capped (benzoyl chloride (2.4 g, 17 mmol) and pyridine (1.7 g, 21 mmol) in 10 mL $CH_2Cl_2$, 20 min.) and dried, giving a substitution of 0.37 mmol/g resin. Synthesis was continued through Fmoc-D-Val as previously indicated for the synthesis of linear viscosin fragment 18. The resin was washed, dried and divided into two equal 0.37 mmol portions. One portion was removed for use in the synthesis of [D-Thr$^7$]-viscosic acid 6. The remaining 0.37 mmol was continued through Fmoc-OBzl-D-Glu as previously indicated for the synthesis of linear viscosin fragment 18. At this point the rein was deblocked with piperidine (50% in DMF, 5 min) and coupled for 6 h with a solution of Fmoc-L-Leu-Pfp [formed by reaction of Fmoc-L-Leu (480 mg, 0.92 mmol), DCC (190 mg, 0.92 mmol) and pentafluorophenol (203 mg, 1.10 mmol) in 10 mL DMF (30 min)]. Synthesis was completed by piperidine deblock (20 min.) and coupling for 2 h with pentafluorophenyl D-3-hydroxydecanoate (24) (330 mg, 0.93 mmol). The product was cleaved with 50% TFA (30 min), evaporated to dryness and lyophilized from dioxane to yield 670 mg of yellow resinous solid. This was debenzylated as indicated for the synthesis of viscosin 1, and purified by preparative HPLC (PrepPak 1000 cartridge system). A total of 144 mg (34%) of purified 5 was obtained as a white solid. FAB MS m/z: 1166 (M+Na$^+$), 1182 (M+K$^+$).

[D-Thr$^7$]-Viscosic Acid (6)

The 0.37 mmol of Fmoc-D-Val-resin from the above synthesis of viscosic acid was treated in a manner identical to that described for the synthesis of viscosic acid 5, except that Fmoc-D-Thr-Pfp ester 29 was used rather then Fmoc-D-allo-Thr-Pfp ester 27. A total of 575 mg of crude benzyl protected peptide was obtained, which after debezylation as for viscosic acid yielded 290 mg of crude product. Purification by preparative HPLC as indicated for viscosic acid yielded purified 6 as 41 mg (10%) of white solid.

D-3-Hydroxydecanoyl-L-Leu-D-Glu-amide (7)

A total of 2.0 g of 4-methylbenzhydryl amine resin (0.53 mmol N/g resin; resin was in the HCl salt form) was placed in a manual synthesis shaker and washed with DMF (3×10 mL), neutralized with piperidine (50% in DMF, 20 min.) and washed (3×30 mL DMF; 3×20 mL $CH_2Cl_2$). The resin was then coupled quantitatively (Kaiser test) with two Fmoc-OBzl-D-Glu couples [1.22 g (2.65 mmol) Fmoc-OBzl-D-Glu, 550 mg (2.65 mmol) DCC and 400 mg (2.65 mmol) HOBT in 20 mL DMF, 3 h]. The resin was then subjected to a 5 min piperidine deblock and coupled with Fmoc-L-Leu [1.87 g (5.3. mmol) Fmoc-L-Leu, 1.10 g (5.3 mmol) DCC and 800 mg (5.3 mmol) HOBT in 20 mL DMF, 2 h]. The resin was washed, deblocked (5 min., 50% piperidine) and coupled with pentafluoro-D-3-hydroxydecanoate 24 (940 mg, 2.66 mmol) in DMF (20 mL) for 2 h. The resulting resin was washed, dried and treated with 20 mL of anhydrous HF in the presence of 1.8 mL of anisole (0° C., 45 min.). The HF was distilled off and the resin extracted with glacial acetic acid and lyophilized to yield crude 7 as 185 mg white solid. Purification by preparative HPLC (PrepPak 1000 cartridge system) gave a total of 100 mg (22%) of purified 7 was obtained as a white solid. FAB MS m/z: 429 (M+Na+).

EXAMPLE 3

In a continuation of the work with analogs, additional analogs have been prepared which replace the peptide lactone ring of viscosin with a crown ether.

Synthesis

The synthesis of crown ether analogs 10–16 began with commercially available benzo-15-crown-5. For attachment of side-chain moieties, the aryl ring was functionalized first by nitration to the mononitrobenzo-15-crown-5 (30) using 70% $HNO_3$ in $AcOH/CHCl_3$ (94% yield; mp 95°–96° C.; CIMS m/z 314 (M+1); 391 (M+2K+): mp 84°–85° C.).[71] Subsequent reduction of the nitro group to an amine, giving 4'-aminobenzo-15-crown-5 (31), was conducted with ammonium formate/10% Pd.C[26] in modification of a previous synthesis.[71] Although the free amine has been reported as a solid (mp 73°–74° C.),[71] in our hands it proved to be an oil which rapidly darkened over time. The amine was stored by conversion to the hydrochloride salt (dioxane.HCl) giving a white to light blue solid which was stable at room temperature (single peak on reverse phase HPLC, no color change). For subsequent reactions, the hydrochloride salt was converted to the free base immediately prior to use by partioning between aqueous $NaHCO_3/CH_2Cl_2$ and evaporating to dryness.

The preparation of peptide analogs 10–13 utilized amino acids bearing butyloxycarbonyl (Boc) amino protection with carboxyl activation through in situ generated pentafluorophenyl (Pfp) esters.[15] Intermediate mono- and dipeptides 32 and 33 were isolated and characterized before being subjected to amino deprotection using 25% trifluoroacetic acid (TFA) in $CH_2Cl_2$. Preparation of analogs 10 and 11 required the acylation of dipeptide H-L-Leu-OBzl-D-Glu-crown ether (deprotected 33) with D-3-hydroxydecanoic acid Pfp ester 24. The selective acylation of the Leu amino group in the presence of the unprotected hydroxyl on the 3-hydroxydecanoic acid is an example of the differential reactivity of Pfp esters towards amines in the presence of alcohols.[33] Debenzylation of analogs 10, 12 and 14 was carried out catalytically using ammonium formate/10% Pd.C.[26]

Synthesis of 4-carboxyoctadecanoyl derivatives 14 and 15 required the preparation of benzyl-4-carboxyoctadecanoic acid 8. A synthetic route to 8 was employed which utilized the malonic ester synthesis of intermediate adduct 34. Although the reported preparation of a series of di-tert butylalkylmalonates utilized a two-fold excess of malonic ester and 1.5 equivalents of NaH relative to alkylbromide,[72] the present synthesis of 34 used equal quantities of all reactants without apparent problems of serious dialkylation. Structural confirmation of 34 was aided by TFA removal of t-butyl groups to provide known tetradecylmalonic acid.[73,74] Adduct 24 was subject to a Michael addition on benzyl acrylate to give 35. While a study on the addition of alkylmalonic esters (with alkyl substituents ranging from up to 16 carbons) to acrylic esters has reported the use of catalytic quantities of base,[75] care must be taken to exclude extraneous sources of acidic protons which can terminate the catalysis. The crude addition product was treated with TFA, removing the Boc groups to yield diacid 36 which provided fine white crystals from hexane. The decarboxylation of diacid 36 to final product 8 was achieved using moist DMF (1% $H_2O$) at 100°–105° C. overnight in a manner similar to the reported decarboxylation of $\beta$-keto esters.[76] Purification by silica gel flash chromatography and crystallization from acetonitrile gave pure crystalline 8.

BIOLOGICAL

Results and Discussion

It has long been known that certain antibiotics, particularly those of a peptide nature, are capable of increasing the alkali ion permeability of both synthetic and natural lipid membranes.[77,78] Of particular importance in this class of substances are the peptide lactones of which valinomycin and the enniatins are will-studied.[79] Studies of valinomycin, enniatins and related peptides have provided some answers to questions regarding the relationship of peptide structure of their behavior towards membranes.

The possibility exists that the ring portion of viscosin serves as an ionophore in a structurally nonspecific manner. Selectivity and specificity could be imparted by the side chain, which could offer membrane-directed properties. If this were indeed the case, then structurally simple crown ethers, which are well-characterized ionophoric agents,[80] could possibly be substituted for this portion of the molecule. The antimicrobial action of crown ethers is known[81] and certain aspects of valinomycin SAR have been examined by crown ether mimetics having small peptide side chains.[82]

Replacement of the peptide ring of viscosin with a crown ether would result in substantial reduction of synthetic complexity. Biological selectivity would then reside with the attached side chain. A series of crown ether analogs are possible, incorporating those side chain functionalities which are examined in analogs 10–16. Benzo-15-crown-5 ethers 11 and 13 bear the side chains of viscosin 1 and deshydroxy viscosin 3 respectively.

Experimental

Melting points were determined on a MelTemp melting point apparatus and are uncorrected. Fast atom bombardment mass spectra (FAB MS) and chemical ionization mass spectra (CIMS) were determined either at Oneida Research Services, Inc. (Whitesbore, N.Y.) or at the Mass Spectrometry Facility of the University of Maryland Department of CHemistry (College Park, Md.). High-pressure liquid chromatography (HPLC) was performed using a Waters Division of Millipore LC 3000 solvent delivery system equipped with a Rheodyne 7010 injector, a Model 381 variable wavelength detector, a Model 740 data module, and for preparative work, a Water's PrepPak 1000 radial compression module equipped with a Bondapak $C_{18}$ 4.7×30 cm (15–20$\mu$ particle size) cartridge (run at 60 mL/min). Column chromatography was performed using EM Kieselgel 50, 230-14 400 mesh. Combustion analysis were performed at Galbraith Laboratories, Inc. (Knoxville, Tn.) and were within 0.4% of theoretical values unless otherwise indicated.

Synthesis

15-[[N-[(1,1-dimethylethoxy)carbonyl]-0-(phenylmethyl)-D-glutamyl]amino]-2,3,5,6,8,9,11,12-octahydro-1,4,7,10,13-benzopentaoxacyclopentadecin or 4'-[(Boc-OBzl-D-Glu)amino]benzo-15-crown-5 (32)

A solution of Boc-OBzl-D-Glu-Pfp ester was prepared by reacting Boc-OBzl-D-Glu (680 mg, 2.0 mmol), pentafluorophenol (552 mg, 3.0 mmol) and dicyclohexylcarbodiimide (DCC) (412 mg, 2.0 mmol) in 10 mL of $CH_2Cl_2$ (1½ h, rt). Dicyclohexylurea side product was removed by filtration. A total of 2.0 mmol 4'-aminobenzo-15-crown-5 (31) (obtained from the corresponding hydrochloride salt (650 mg) by partitioning between 10% aqueous $NaHCO_3/CH_2Cl_2$ then evaporating to dryness) was dissolved in 10 mL of $CH_2Cl_2$ and added to the Pfp ester solution. The mixture was stirred at rt overnight then evaporated to dryness. The residue was taken up in 10 mL of EtOAc, cooled in ice and filtered to remove residual dicyclohexyl urea. The filtrate was diluted with hexane and cooled, yielding 32 as 640 mg white needles (53%), mp 127°–130° C. Anal. $C_{31}H_{42}N_2O_{10}$:C,H,N.

15-[[N-[N-[(1,1-dimethylethoxy)carbonyl]-L-Leucyl]-0-(phenylmethyl)-D-glutamyl]amino]-2,3,5,6,8,9,11,12-octahydro-1,4,7,10,13-benzopentaoxacyclopentadecin or 4'-[(Boc-L-Leu-OBzl-D-Glu)amino]benzo-15-crown-5 (33)

A solution of Boc-L-Leu-Pfp ester was prepared by reacting Boc-L-Leu (42 mg, 180 μmol), pentafluorophenol (33 mg, 180 μmol) and DCC (37 mg, 180 μmol) in 1.0 mL of $CH_2Cl_2$ (2 h, rt). Dicyclohexylurea was removed by filtration. Crown ether 32 (100 mg, 170 μmol) was stirred in 25% $TFA/CH_2Cl_2$ (4 mL, 30 min, rt), then taken to dryness by rotary evaporation. The residue was taken up in $CH_2Cl_2$ (2 mL) then treated with excess triethylamine (660 mg, 6.6 mmol) and combined with the Boc-L-Leu-Pfp ester solution. After stirring at rt for 3 h, the mixture was taken to dryness by rotary evaporation, giving a colorless oil which was purified first by silica gel chromatography (200 g of silica in a 5 cm dia. column eluted first with 100% $CH_2Cl_2$, then with $Ch_2Cl_2$: methanol (9:1)) then by preparative HPLC ($H_2O$:acetonitrile gradient) to yield product 33 as a white solid (70 mg, 67%), mp 123°–125° C. (shrinks at 60° C.). Anal. $C_{37}H_{52}H_3O_{11}.\frac{1}{2}H_2O$:C,H,N.

15-[[N-[N-[D-3-Hydroxydecanoyl]-L-Leucyl]-0-(phenylmethyl)-D-glutamyl]amino]-2,3,5,6,8,9,11,12-octahydro-1,4,7,10,13-benzopentaoxacyclopentadecin or 4'-[(D-3-hydroxydecanoyl-L-Leu-OBzl-D-Glu)amino]-benzo-15-crown-5 (10)

Crown ether 33 (450 mg, 630 μmol) was stirred in 25% $TFA/CH_2Cl_2$ (10 mL, 30 min, rt) then taken to dryness by rotary evaporation. The residue was then stirred in $CH_2Cl_2$ (10 mL, 3 h, rt) with pentafluorophenyl D-3-hydroxydecanoate 24 (220 mg, 630 μmol) and triethylamine (656 mg, 6.53 mmol). The reaction mixture was taken to dryness by rotary evaporation and purified by silica gel chromatography (200 g silica gel in a 5 cm dia. column eluted first with 100% $CH_2Cl_2$, then with $CH_2Cl_2$: methanol (97.5:2.5)) then by preparative HPLC ($H_2O$:acetonitrile gradient) to yield product 10 as a white solid (235 mg, 47%). A second purification by prep HPLC was performed to obtain analytically pure material (45 mg, 9% overall yield), mp 120° C. (shrinks at 105° C.). CIMS ($NH_3$) m/z:786 (M+1); 803 (M+$NH_4$). Anal. $C_{42}H_{63}N_3O_{11}.2H_2O$:C,H,N.

15-[[N-[N-[D-3-Hydroxydecanoyl]-L-Leucyl]-D-glutamyl]amino]-2,3,5,6,8,9,11,12-octahydro-1,4,7,10,13-benzopentaoxacyclopentadecin or 4'-[(D-3-hydroxydecanoyl-L-Leu-D-Glu)amino]benzo-15-crown-5 (11)

A mixture of crown ether 10 (197 mg, 250 μmol), ammonium formate (158 mg, 2.5 mmol) and 10% Pd.C (197 mg) was stirred in methanol (50 mL, 1½ h, rt) then filtered and evaporated to dryness. Purification by preparative HPLC (0.1% TFA in a $H_2O$:acetonitrile gradient system) yielded product 11 as a white solid (64 mg, 36%), mp 164°–167° C. CIMS ($NH_3$) m/z:695 (M+1); 713 (M+$NH_4$). Anal. $C_{35}H_{57}N_3O_{11}.H_2O$:C,H,N.

15-[[N-[N-[Decanoyl]-L-Leucyl]-0-(phenylmethyl)-D-glutamyl]amino]-2,3,5,6,8,9,11,12-octahydro-1,4,7,10,13-benzopentaoxacyclopentadecin or 4'-[(Decanoyl-L-Leu-OBzl-D-Glu)amino]benzo-15-crown-5 (12)

Crown ether 33 (450 mg, 630 μmol) was stirred in 25% $TFA/CH_2Cl_2$ (10 mL, 30 min, rt) then taken to dryness by rotary evaporation. The residue was dissolve in $CH_2Cl_2$ (5 mL) and triethylamine added (656 mg, 6.53 mmol). Decanoic acid (210 mg, 630 μmol), pentafluorophenol (120 mg, 630 μmol) and DCC (130 mg, 630 μmol) were stirred in $CH_2Cl_2$ (20 mL, 3 h, rt) then cooled in ice and dicyclohexyl urea removed by filtration. The filtrate was combined with the solution of deblocked 12 and stirred (3 h, rt) then evaporated to dryness and purified by preparative HPLC ($H_2O$:acetonitrile gradient) to yield product 12 as a white solid (80 mg, 16%), mp 150° C. (shrinks at 120° C.). CIMS ($NH_3$) m/z:770 (M+1); 787 (M+$HN_4$). Anal. $C_{42}H_{63}N_3O_{10}.H_2O$:C,H,N.

15-[[N-[N-[Decanoyl]-L-Leucyl]-D-glutamyl]amino]-2,3,5,6,8,9,11,12-octahydro-1,4,7,10,13-benzopentaoxacylopentadecin or 4'-[(Decanoyl-L-Leu-D-Glu)amino]benzo-15-crown-5 (13)

A mixture of crown ether 12 (240 mg, 310 μmol), ammonium formate (197 mg, 3.1 mmol) and 10% Pd.C (240 mg) was stirred in methanol (50 mL, 4 h, rt) then filtered and evaporated to dryness. Purification by preparative HPLC ($H_2O$:acetonitrile gradient) yielded product 13 as a white solid (30 mg, 14%). CIMS ($NH_3$) m/z:679 (M+); 697 (M+$NH_4$). Anal. $C_{35}H_{57}N_3O_{10}.1\frac{1}{2}H_2O$:C,H,N.

di-(Dimethylethyl)-n-tetradecylmalonate 34

A suspension of di-tert butyl malonate (10.80 g, 50 mmol) and t-BuOK (5.60 g, 50 mmol) was stirred (30 min, 75° C.) in t-BuOH (150 mL, dried over 4 Å sieves). To this was added a solution of 1-bromotetradecane (13.85 g, 50 mmol) and the reaction stirred at 75° C. overnight. Solvent was removed by rotary evaporation, giving a white semi-solid, which was partitioned between $CH_2Cl_2$ (100 mL) and saturated aqueous NaCl (2×300 mL), dried ($MgSO_4$) and evaporated to a colorless oil (15.3 g). Purification by silica gel flash chromatography (100% hexane incremented to hexane:$CH_2Cl_2$ (70:30)) gave product 34 as a colorless oil (10.0 g, 48%).

High resolution FAB MS:$C_{25}H_{49}O_4$ (M+H); Theor. 413.3630855. Found 413.3627625.

A sample of 34 was treated with 100% TFA (10 min) then crystallized in hexane, yielding known n-tetradecylmalonate, mp 118°–121° C. (lit. mp 118°–120° C.; 123°–124° C.).

Benzyl-4,4-dicarboxyoctadecanoate 36

To a solution of di-(dimethylethyl)-n-tetradecylmalonate 34 (4.12 g, 10.0 mmol) and t-BuOK (244 mg, 2.0 mmol) in t-BuOH (10 mL, dried over 4 Å sieves) was added a solution of benzyl acrylate (1.62 g, 10.0 mmol in 5 mL t-BuOH). The initially colorless solution immediately turned brown. It was stirred (3 h, rt) then additional t-BuOK (112 mg, 1.0 mmol) was added and the reaction continued overnight. The mixture was neutralized with AcOH then evaporated to dryness and treated with neat TFA (20 mL, 1 h). The TFA was removed by rotary evaporation, the residue dissolved in warm hexane, treated with activated charcoal then filtered. The filtrate provided fine white crystals which proved to be pasty when filtered. Drying provided product 36 as a white solid (2.31 g, 50%), mp 47°–49° C. High resolution FAB MS:$C_{27}H_{43}O_6$(M+H); Theor. 463.307147. Found 463.3059 646. Anal. $C_{27}H_{42}O_6 \cdot \frac{1}{2}H_2O$:C,H.

Benzyl-4-carboxyoctadecanoate 8

A solution of benzyl-4,4-dicarboxyoctadecanoate 36 (1.14 g, 2.5 mmol) in moist DMF (100 mL DMF; 1 mL $H_2O$) was stirred for 2 days (100°–105° C.) then solvent was removed by rotary evaporation. Crystallization from hexane yielded product 8 as a white solid (950 mg, 91%), mp 62°–63° C. High resolution FAB MS: $C_{26}H_{43}O_4$(M+H); Theor. 419.3161353. Found 419.3144060. Anal. $C_{26}H_{42}O_4$:C,H.

15-[2-[Benzyl-3-propanoyl]hexadecanoyl]amino]-2,3,5,6,8,9,11,12-octahydro-1,4,7,10,13-benzopentaoxacyclopentadecin (14)

A solution of benzyl-4-carboxyoctadecanoate 8 (318 mg, 760 μmol), pentafluorophenol (110 mg, 600 μmol) and DCC (160 mg, 780 μmol) was stirred in 4 mL of $CH_2Cl_2$ (½ h, rt). Dicyclohexylurea side product was removed by filtration. A total of 500 μmol of aminobenzo-15-crown- 5 (31) (obtained from the corresponding hydrochloride salt (160 mg) by partitioning between 10% aqueous $NaHCO_3/CH_2Cl_2$ then evaporating to dryness) was dissolved in 4 mL of $CH_2Cl_2$ and added to the Pfp ester solution. The mixture was stirred at rt overnight then evaporated to dryness. Purification by preparative HPLC (0.1% TFA in a $H_2O$:acetonitrile gradient system) yielded product 14 as a white solid (350 mg, 100%). FAB MS m/z:684 (M+1): 632 (M−Bzl+K+); 594 (M+1−Bzl).

15-[2-[3-propanoyl]hexadecanoyl]amino]-2,3,5,6,8,9,11,12-octahydro-1,4,7,10,13-benzopentaoxacyclopentadecin (15)

A mixture of crown ether 14 (137 mg, 200 μmol), ammonium formate (126 mg, 2.0 mmol) and 10% Pd.C (50 mg) was stirred in methanol (10 mL, 2 h, rt) then filtered, evaporated to dryness and partitioned between dilute aqueous HCl (30 mL) and $CHCl_3$ (2×30 mL). The organic phase was dried ($MgSO_4$), evaporated to dryness and lyophilized from dioxane yielding 15 as a white solid (84 mg, 71%), mp 70°–75° C. (shrinks at 40° C.). CIMS ($NH_3$) m/z:594 (M+1); 611 (M+$NH_4$).

FAB MS m/z: 594 (M+1); 616 (M+Na+) Anal. $C_{33}H_{55}NO_8 \cdot 2H_2O$:C,H,N.

EXAMPLE 4

Biological

Lysis

For the purpose of determining the ability of the compounds to lyse the parasite *Leishmania donovani*, the parasites were harvested from culture medium M199+5% fetal bovine serum (FBS), washed twice in Hanks Balanced Salts Solution (HBSS) and resuspended in same at $1 \times 10^8$ per mL. The requisite amount of compound at a concentration of 10 mg/mL in water (compounds 1, 9, and 10) or in ethanol was added and the cultures examined at 4 h and after overnight at 27° C.

Growth

For the purpose of determining the effect of the compounds on the growth of parasite in serum-containing and serum-free medium, the parasites were harvested from culture medium M199+5% FBS, washed twice in HBSS and resuspended in same at $1 \times 10^8$/mL. Serum-containing M199 ans serum-free REIII media were filtered and sterilized prior to use. The washed cells were added to achieve an initial concentration of $1.66 \times 10^6$ cells/mL. Cell densities were determined by hemacytometry at 21 h, and in some cases at 43 h of incubation at 27° C.

TABLE I

| | Lowest concentration with activity against *L. Donovani* | | |
|---|---|---|---|
| Compound[1] | Lysis mg/ml | Growth mg/ml | Growth (Serum Free Medium) mg/ml |
| 1 | 100 | 100 | 100 |
| 4 | NOT TESTED -- insoluble in water | | |
| 5 | NO EFFECT | | |
| 6 | NO EFFECT | | |
| 7 | NO EFFECT | | |
| 14 | 30 | 100 | 10 (Lowest Effective |
| 15 | 30 | 30 | 10 Conc. being |
| 10 | 30 | 100 | 100 determined) |
| 11 | NO EFFECT | | |
| 12 | 100 | NO EFFECT ON GROWTH (May have come out of solution and filtered out) | |
| 13 | NO EFFECT | | |

[1] As numbered in Examples.

It is understood that these descriptions, examples and embodiments are for illustrative purposes only, and that various modifications would be suggested within the spirit and purview of this application and the scope of the appended claims.

REFERENCES CITED IN THE EXAMPLES:

1. Groupe, V., et al., *Proc. Soc. Exptl. Biol, Med.* 78:354–358 (1951)
2. Kochi, M., et al., *Bact. Proc.* 29–30 (1951)
3. Ohno, T., et al., *J. Agr. Chem. Soc, Japan.* 27:665–669 (1953) (CA 49:3012d (1955)
4. Hiramoto, M., et al., *Biochem, Biophys, Res. Commun.* 35:702–706 (1969)
5. Hiramoto, M., et al., *Tetrahedron Lett.* 13:1087–1090 (1970)
6. Rinehart, K. L., et al., *J. Amer. Chem. Soc.* 109:6846–6848 (1987)

7. Carpino, L. A., et al., *J. Amer. Chem. Soc.* 92:5748–5749 (1970)
8. Wang, S. S., *J. Amer. Chem. Soc.* 95:1328–1333 (1973)
9. Shute, R. E., et al., *Tetrahedron Lett.* 28:3419–3422 (1987)
10. Paguet, A., *Can. J. Chem.* 60:976–980 (1982)
11. Wang, S. S., *J. Org. Chem.* 40:1235–1239 (1975)
12. Konig, W., et al., *Chem. Ber.* 103:788–798 (1970)
13. Kaiser, R. L., et al., *Anal. Biochem.* 34:595–598 (1970)
14. Stewart, J. M., et al., 153rd Annual Meeting of the American Chemical Society, April 1967
15. Kisfaludy, L., et al., *Synthesis* 325–327 (1983)
16. Elliot, D. F., *J. Chem. Soc.* 62–68 (1950)
17. Levy, D., et al., *Biochemistry* 9:3215–3222 (1970)
18. Mauger, A. B., et al., *Int. J. Peptide Protein Res.* 30:481–488 (1987)
19. Gilon, C., et al., *Tetrahedron Lett.* 40:3811–3814 (1979)
20. Hubert, A. J., et al., *Helv. Chim. Acta* 46:1429–1445 (1963)
21. Cartwright, N. J., *Biochem. J.* 67:663–669 (1957)
22. Rathke, M. W., et al., *J. Amer. Chem. Soc.* 95:3050–3051 (1973)
23. DeTar, D. F., et al., *J. Amer. Chem. Soc.* 88:1013–1019 (1956)
24. Khorana, H. G. *Chem. Rev.* 53:145–166 (1953)
25. Shute, R. E., et al., *J. Med. Chem.* 30:71–78 (1987)
26. Anwer, M. K., et al., *Synthesis* 929–932 (1980)
27. Sheehan, J. C., et al., *J. Amer. Chem. Soc.* 95:875 (1973)
28. Rinehart, K. L., et al., *J. Amer. Chem. Soc.* 109:6846 (1987)
29. Gisin, B. F., et al., *J. Amer. Chem. Soc.* 91:2691 (1969)
30. Okada, K., et al., *Chem. Pharm. Bull.* 22:2136 (1974)
31. Carpino, L. A., et al., *J. Amer. Chem. Soc.* 92:5748 (1970)
32. Atherton, E., et al., *Tetrahedron* 44:843 (1988)
33. Kisfaludy, L., et al., Peptides, structure and function, Proceedings of the ninth American Peptide Symposiu, Weber, Hruby and Kopple ed., Pierce Chemical Co., Rockford, Ill. (1985)
34. Fuller, W. D., et al., Peptides structure and function, Proceedings of the eight American peptide symposium, Hruby and Rich ed., Pierce Chemical Co., Rockford, Ill. (1983)
35. Hintzer, K., et al., *J. Org. Chem.* 47:3850 (1982)
36. Bodanzky, J. M., et al., *J. Amer. Chem. Soc.* 89:6753 (1967)
37. Stewart, J. M., The peptides, analysis, synthesis and biology Gross and Meienhofer ed., Academic Press, New York, N.Y. (1981)
38. Schon, I., et al., *Synthesis* 303 (1986)
39. Diago-Mesguer, J., et al., *J. Org. Chem.* 44:3101 (1980)
40. Greer, D. A., *Texas Health Bull* 9:11 (1955)
41. Schiffler, R. J., et al., *Amer. Med. Assoc.* 251:2983 (1984)
42. Keierszenbaum, F., *Trop. Med. Parasit*, Mansfield ed., Marcel Dekker, New York (1984)
43. Albericio, F., et al., *Int. J. Peptide Protein Res.* 23:342 (1984)
44. Matsueda, G. R., et al., *Peptides* 2:45 (1978)
45. Brockmann, H., et al., *Chem. Ber.* 88:57 (1955)
46. Gaumann, E., et al., *Exper.* 3:202 (1947)
47. Horton, J. M., et al., Antimicrobial Therapy, Ristuccia and Cunha ed., Raven Press, New York, N.Y. (1984)
48. Rosenthal, K. S., et al., *Antimicrob. Ag. Chem.* 12:665 (1977)
49. Benz, F., et al., *Helv. Chim. Acta.* 57:2459 (1974)
50. Donovan, J. J., et al., *Proc. Natl. Acad. Sci. USA* 78:172 (1981)
51. Bhakdi, S., et al., *Phil. Trans. R. Soc. Lond, B.* 306:311 (1984)
52. Merrifield, R. B., et al., *Biochem.* 21:5020
53. Zasloff, M., et al., *Proc. Natl. Acad. Sci. USA* 85:910 (1988)
54. Giovannini, M. G., et al., *Biochem. J.* 243:113 (1987)
55. Mercado, T. I., et al., *Antimicrob. Agents Chemother.* 22:1051 (1982)
56. Jaynes, J. M., et al., *FASEB J.* 2:2878 (1988)
57. Ouaissi, M. A., *Science* 234:603 (1986)
58. Timm, S. L., *Comp. Biochem. Physiol.* 71B:397 (1982)
59. Bone, G. J., et al., *J. Gen. Microbiol.* 31:261 (1963)
60. Cunningham, L. A., et al., *J. Gen. Microbiol.* 70:491 (1972) p0 61. Balis, J., *Revue d'Elevage et de Medicine Veterinare des Pays Tropical* 19:351 (1966)
62. Godfrey, D. G., *Exp. Parasitol.* 7:255 (1958)
63. Tosteson, D. C., *J. Gen. Physiol.* 50:2513 (1967)
64. Vining, L. C., et al., *Can. J. Chem.* 40:1579 (1962)
65. Storm, D. R., et al., *Ann. Rev. Biochem.* 46:723 (1977)
66. Citri, N., et al., *Bull. Res. Council Israel* 4:210 (1954)
67. Gaur, R. K., et al., *Ind. J. Chem.* 27B:405 (1988)
68. Volger, K., et al., *Helv. Chim. Acta.* 47:526 (1964)
69. Chang, C., et al. *Int. J. Pept. Res.* 15:59 (1980)
70. Stewart, J. M. et al., Pierce Chemical Co., Rockford, Ill. (1984)
71. Ungaro, R., et al., *J. Amer. Chem. Soc.* 98:5198 (1976)
72. Fonken, G. S., et al., *J. Amer. Chem. Soc.* 74:831 (1952)
73. Asano, M., et al., *J. Parm. Soc. Jpn.* 61:220 (1941)
74. Chargaft, E., *Chem. Ber.* 65B:745 (1932)
75. Floyd, D. E., et al., *J. Org. Chem.* 16:882 (1951)
76. Paine, J. B., et al., *J. Org. Chem.* 41:3857 (1976)
77. Pressman, B. C., et al., *Proc. Natl. Acad. Sci. USA* 58:1949 (1967)
78. Tosteson, D. C., *Fed. Proc.* 27:1269 (1968)
79. Shemyakin, M. M., et al., *Experentia* 19:566 (1963)
80. Pedersen, C. J., *Science* 241:536 (1988)
81. Yagi, K., et al., *J. Inclusion Phenom.* 2:179 (1984)
82. White, B. D., et al., *J. Org. Chem.* 54:939 (1989)

What is claimed is:

1. Peptidomimetics viscosin analogue having the following formula:

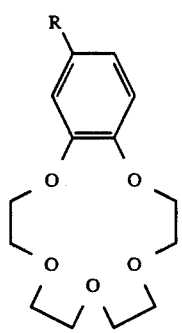

2. A pharmaceutical composition comprising the viscosin analog of claim 1 and a pharmaceutically acceptable carrier.

* * * * *

UNITED STATES PATENT AND TRADEMARK OFFICE
CERTIFICATE OF CORRECTION

PATENT NO. : 5,169,862

DATED : December 8, 1992

INVENTOR(S) : Burke, Jr., et al

It is certified that error appears in the above-indentified patent and that said Letters Patent is hereby corrected as shown below:

Replace "ile" with -- Ile -- at the following locations:

column 2, at line 60;

column 3, at lines 5 and 25;

in the chemical structure bridging column 5 and 6; and in the structures labelled 4, 17 and 19 in columns 5-8.

Column 3, lines 21-29, the four asterisks should be deleted--.

UNITED STATES PATENT AND TRADEMARK OFFICE
CERTIFICATE OF CORRECTION

PATENT NO. : 5,169,862
DATED : December 8, 1992
INVENTOR(S) : Burke, Jr., et al

It is certified that error appears in the above-indentified patent and that said Letters Patent is hereby corrected as shown below:

Column 28, lines 49-64, claim 1, add:

Wherein R is

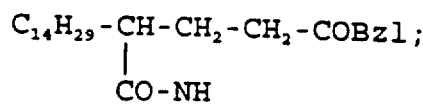

or

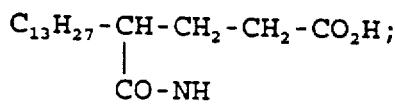

wherein Bzl is benzyl.

Signed and Sealed this

Nineteenth Day of July, 1994

*Attest:*

BRUCE LEHMAN

*Attesting Officer*     *Commissioner of Patents and Trademarks*